(12) United States Patent
Jaber (10) Patent No.: US 9,241,822 B2
(45) Date of Patent: Jan. 26, 2016

(54) PORTABLE CERVICAL TRACTION DEVICE

(71) Applicant: KING ABDULAZIZ UNIVERSITY, Jeddah (SA)

(72) Inventor: Hassan M. H. Jaber, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 345 days.

(21) Appl. No.: 13/732,259

(22) Filed: Dec. 31, 2012

(65) Prior Publication Data

US 2014/0188027 A1    Jul. 3, 2014

(51) Int. Cl.
| | |
|---|---|
| A61F 5/00 | (2006.01) |
| A61F 5/048 | (2006.01) |
| A61F 5/04 | (2006.01) |
| A61F 5/042 | (2006.01) |

(52) U.S. Cl.
CPC . *A61F 5/048* (2013.01); *A61F 5/04* (2013.01); *A61F 5/042* (2013.01)

(58) Field of Classification Search
CPC ........... A61F 5/04; A61F 5/042; A61F 5/048; A61F 5/026; A61H 1/0218; A61H 2203/0406; E05C 1/0004; E05C 1/04; E05C 1/06; E05C 1/02; Y10T 24/45005; Y10T 24/45089
USPC .............. 403/319, 324, 401–402; 602/32
See application file for complete search history.

(56) References Cited

U.S. PATENT DOCUMENTS

| | | | |
|---|---|---|---|
| 2,706,982 A | 4/1955 | Hale et al. | |
| 3,359,976 A * | 12/1967 | Laval, Jr. | ........................ 602/36 |
| 3,795,243 A | 3/1974 | Miller | |
| 3,915,161 A | 10/1975 | Shields | |
| 4,250,874 A | 2/1981 | Rude | |
| 4,305,611 A * | 12/1981 | Robins | .......................... 292/238 |
| 4,539,979 A | 9/1985 | Bremer | |
| 5,010,898 A | 4/1991 | De Kanawati et al. | |
| 5,108,042 A * | 4/1992 | Puryear et al. | ................. 242/288 |
| 5,242,377 A * | 9/1993 | Boughner et al. | ............... 602/17 |
| 5,411,471 A * | 5/1995 | Terrazas | .................. A61F 5/055 2/421 |
| 6,447,468 B1 | 9/2002 | Hankins et al. | |
| 6,733,470 B1 * | 5/2004 | DeGeorge et al. | ............... 602/32 |
| 7,150,140 B2 * | 12/2006 | Harmon | ............................ 57/59 |

FOREIGN PATENT DOCUMENTS

WO    WO 94/24966    11/1994

* cited by examiner

*Primary Examiner* — Nicholas Woodall
*Assistant Examiner* — Camtu Nguyen
(74) *Attorney, Agent, or Firm* — Richard C. Litman (57) ABSTRACT

The portable cervical traction device includes a brace having at least a pair of shoulder hooks configured to be worn over the shoulders and on the back of a user. A traction control mechanism is attached to the brace and includes an L-shaped traction bar. A plurality of hooks is attached to the traction bar, and a head sling can be attached to selected hooks for comfortable and proper support of the user's head. The traction control mechanism selectively raises or lowers the traction bar to apply the desired traction on the user. Since the brace is portable, the portable cervical traction device provides greater mobility for the user while maintaining proper traction. The degree of traction can be easily adjusted to account for the degree of recovery of the user.

20 Claims, 9 Drawing Sheets

PORTABLE CERVICAL TRACTION DEVICE

BACKGROUND OF THE INVENTION

1. Field of the Invention

The present invention relates to medical braces, and particularly to a portable cervical traction device providing freedom of mobility for the user while maintaining necessary traction of the affected malformed or injured area of the body.

2. Description of the Related Art

Patients with neck pain due to muscle strain from various causes, including bad posture during sleep or sitting, as well as from degenerative processes and disc diseases, benefit from intermittent cervical traction. Currently, traction is usually applied in bed or in physiotherapy departments.

Several solutions exist for applying traction. One solution includes a home cervical traction set that requires the user to sit on a chair against a door while the traction force is applied by weights hanging over the door by a rope connected to a head halter or strap. This is a cumbersome contraption that requires much in terms of physical activity for preparing the device, which can be extremely difficult for the user requiring such treatment. Moreover, it would be a difficult task to prepare by oneself.

Other solutions include various forms of portable appliances. For example, patients with cervical injury must be transported carefully with a rigid collar. However, the collar does not provide enough traction. Another example involves patients with cervical dislocations, which usually confines them to bed. Various braces, such as the halo brace and the SOMI (sternal occipital mandibular immobilizer) brace, apply some degree of traction. However, they are very difficult to adjust or modify the degree of necessary traction.

In light of the above, it would be a benefit in the art of medical braces to provide a cervical brace that is portable and has easily adjustable traction for greater freedom of mobility for the user while maintaining the necessary traction. Thus, a portable cervical traction device solving the aforementioned problems is desired.

SUMMARY OF THE INVENTION

The portable cervical traction device includes a brace having at least a pair of shoulder hooks configured to be worn over the shoulders and on the back of a user. A traction control mechanism is attached to the brace and includes an L-shaped traction bar. A plurality of hooks is attached to the traction bar, and a head halter sling can be hung on selected hooks for comfortable and proper support of the user's head. The traction control mechanism selectively raises or lowers the traction bar to apply the desired traction on the user. Since the brace is portable, the portable cervical traction device provides greater mobility for the user while maintaining proper traction. The degree of traction can be easily adjusted to account for the degree of recovery from the user. This device could be used by a nonprofessional, unless there is a confirmed or suspected cervical spine fracture or dislocation, and then its application is strictly restricted to medical doctors with extra protection of a collar.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
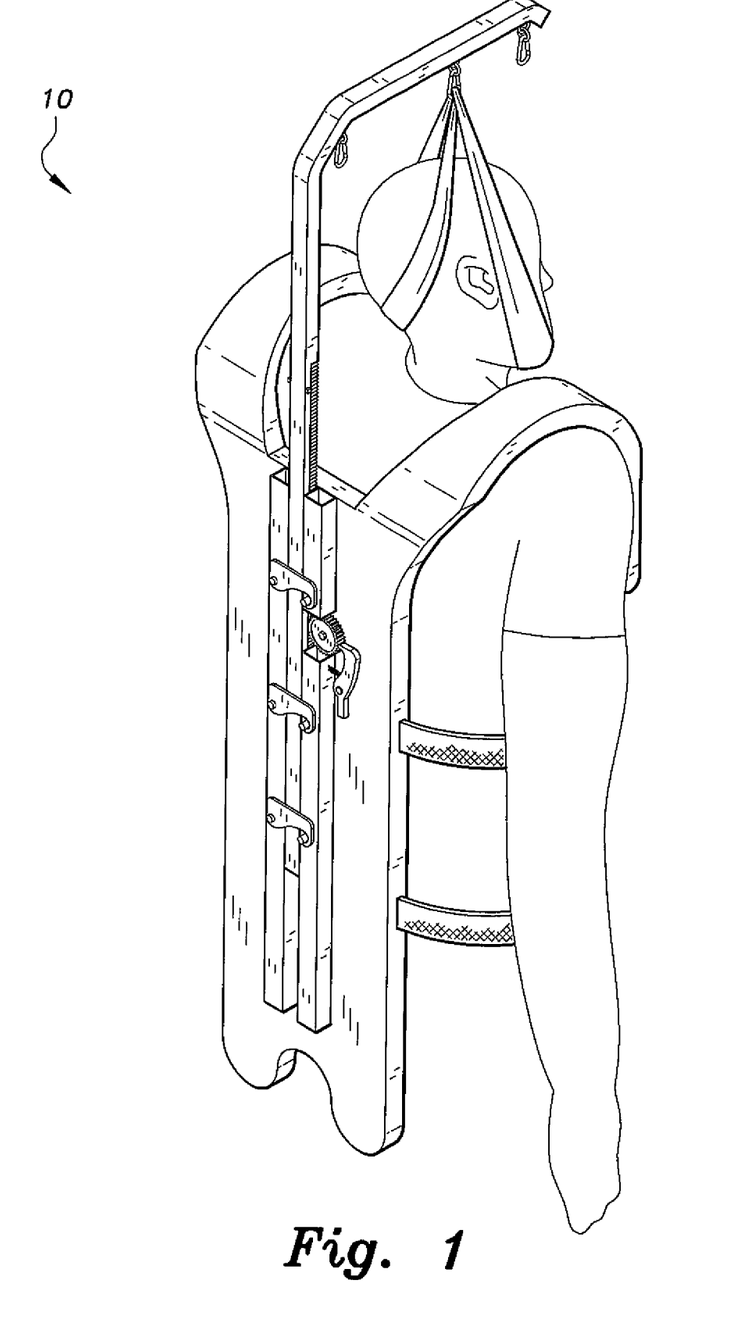
FIG. 1 is an environmental, perspective view of a portable cervical traction device according to the present invention.
Figure 2:
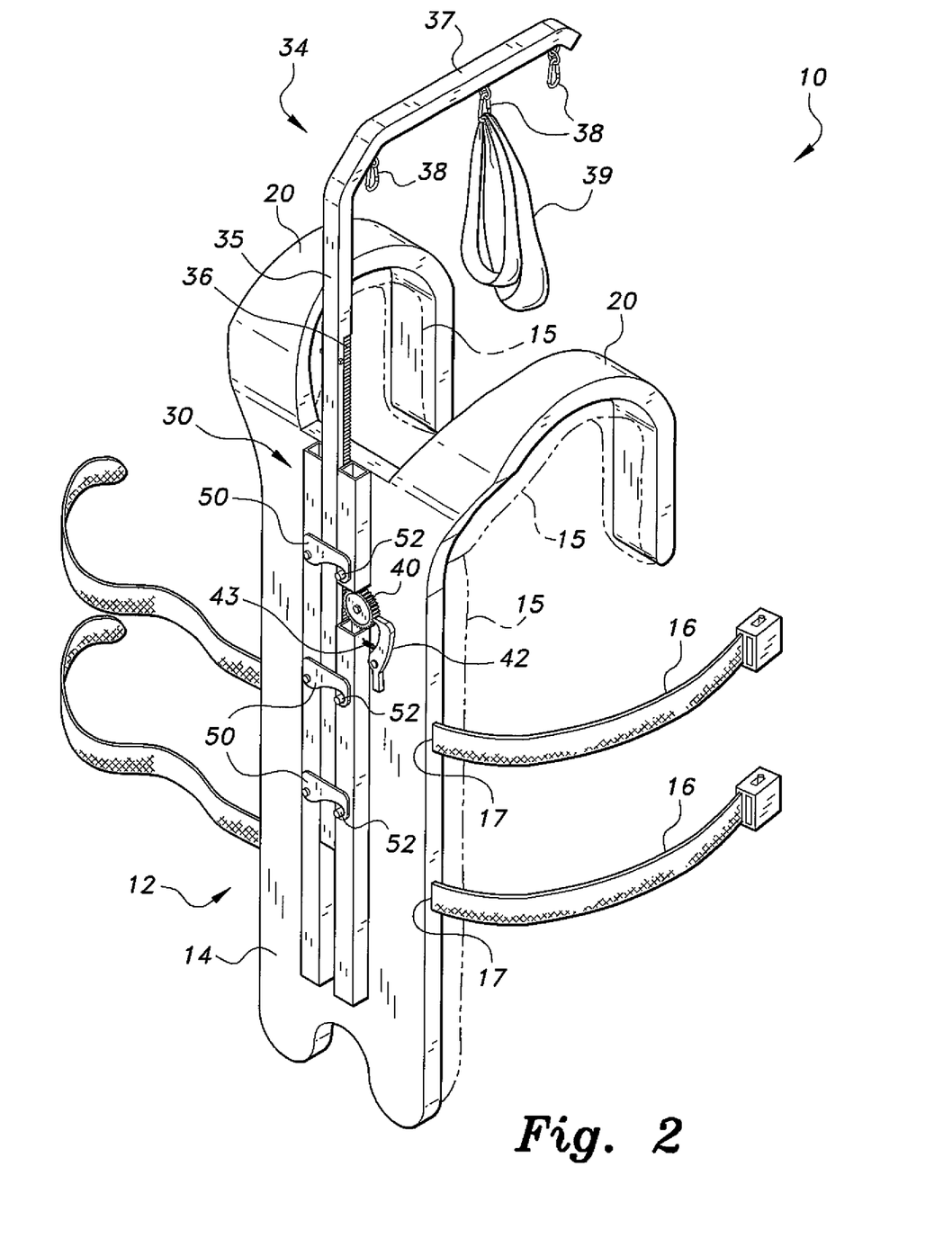
FIG. 2 is a perspective view of the portable cervical traction device of FIG. 1.
Figure 3:
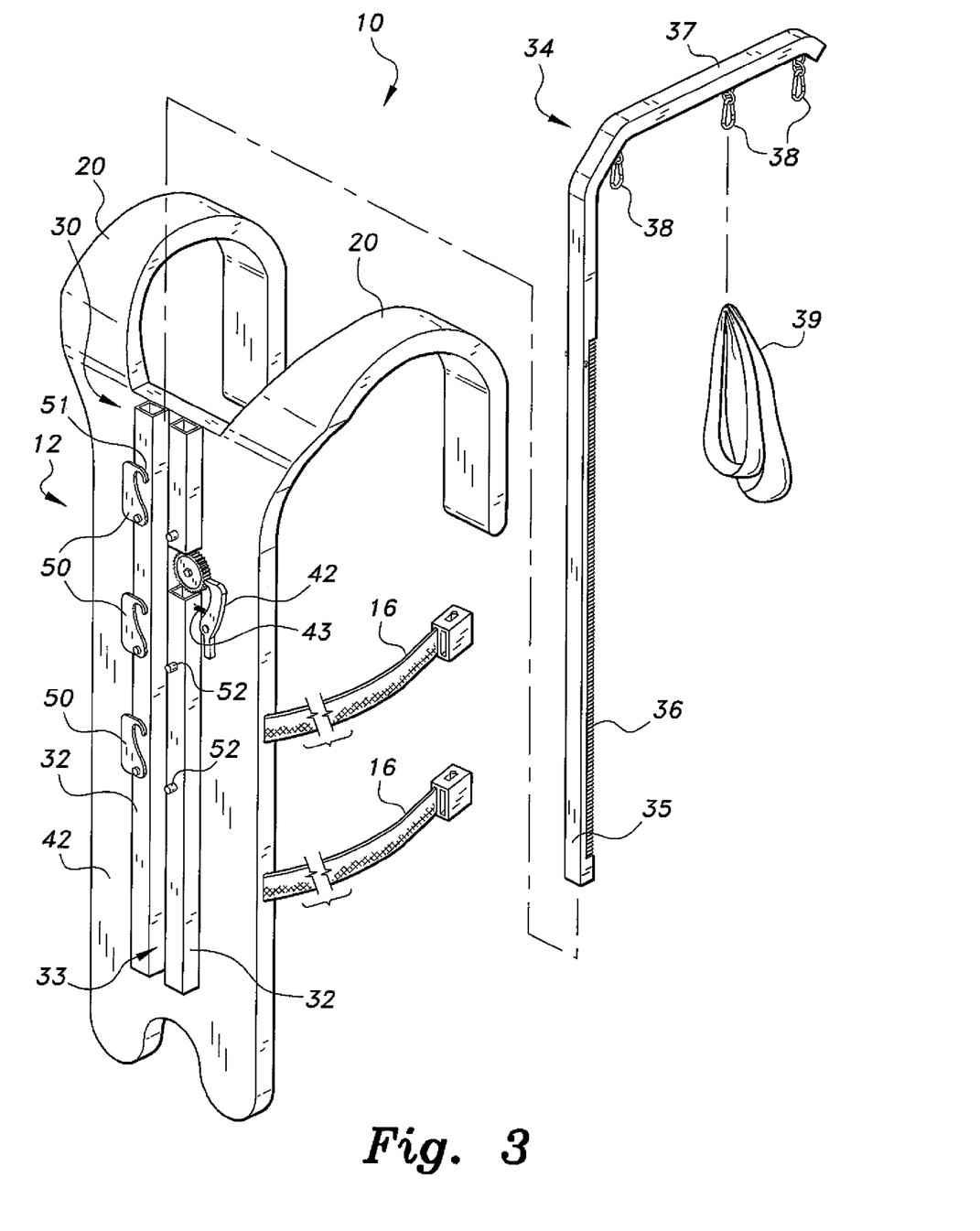
FIG. 3 is a partially exploded view of the portable cervical traction device of FIG. 1.

The portable cervical traction device, a first embodiment of which is generally referred to by the reference number 10, provides the user with greater mobility than conventional devices while maintaining proper traction and providing easy-to-wear and adjustable traction control for the user. As shown in FIGS. 1-3, the portable cervical traction device 10 includes a brace 12 configured to be worn on the back of a user. The brace 12 is preferably constructed from rigid materials (such as wood, plastic, metal, composites and combinations thereof) so that the brace 12 is relatively stiff against the body of the user when worn. The portable cervical traction device 10 must exhibit some degree of stiffness for proper traction control. However, the brace 12 can be constructed with some flexibility for increased comfort. Additionally, the brace 12 can be more ergonomically contoured in order to conform to the shape of the user's back.

One exemplary construction of the brace 12 can include a stiff outer shell having a padded or cushioned layer on one side. FIG. 2 also shows an example of padding 15 that can be placed at selected portions of the brace 12 in contact with the body of the user, i.e., the back side of the brace 12, for even more comfort, especially for extended periods of use. Moreover, the padding 15 can extend further around the user's neck area to serve as a head rest.

The brace 12 includes an elongate back section 14 and at least a pair of shoulder straps hooks 20 extending from the corners of the back section 14. The back section 14 preferably spans about the same length of the user's back and is relatively straight. These features provide stability and promote proper alignment of the spine. Alternatively, the back section can be slightly curved in the vertical direction, corresponding to the proper curvature of the back of the user. At least a pair of releasable straps 16 can be provided on the brace 12 to secure the brace 12 onto the user's body when placed on the back of the user. The straps 16 loop around the front of the user's torso, and the combination of the straps 16 and the shoulder hooks 20 securely mounts the portable cervical traction device 10 onto the user's body. The straps 16 can be threaded through corresponding slots 17 on the sides of the brace 12 (as best shown in FIG. 2) or secured thereon by various conventional means, e.g., loops, hooked fasteners, and the like.

In order to facilitate proper traction, the portable cervical traction device 10 includes an adjustable traction control mechanism 30 disposed on the brace 12. The traction control mechanism 30 includes a pair of spaced, elongate rails 32 disposed in parallel along the length of the back section 14. These rails 32 define a guide channel 33 therebetween, which together form a guide rail for an elongate traction bar 34. The guide rail can be constructed in parts, as shown, or as a single molded unit detachably mounted or fixed to the back section 14.

The traction bar 34 is constructed as an L-shaped, vertical bar having an elongate rack section 36 disposed on the long member 35 and a plurality of loops or hooks 38 disposed along the length of the horizontal cross member 37. Each hook 38 is set at selected locations along the cross member 37 for hanging a head halter or sling 39 thereon. The hooks 38 permit the user or physician to select the best hook 38 for properly positioning and supporting the user's head.

In place of conventional traction means, such as weights, the traction is applied by vertical adjustment of the traction bar 34. The adjustment mechanism includes the rack gear section 36 and a drive pinion 40 disposed in a gap on one of the rails 32. The drive pinion 40 engages teeth on the rack section 36, and selective rotation of the drive pinion 40 raises or lowers the traction bar 34 to the desired height of the cross member 37. The rotated position of the drive pinion 40 is locked or set by a pawl or latch hook 42, which is pivotally mounted to the back section 14 and biased by a spring 43. The spring-biased pawl 42 maintains and locks the adjusted position of the traction bar 34.

In use, the combination of the head sling 39 and proper height adjustment of the traction bar 34 exerts the proper or desired amount of tension for traction. Moreover, the above arrangement permits easy adjustments as needed during the course of recovery. Additionally, since the traction control mechanism is directly attached to the brace 12, the user can safely wear the portable cervical traction device 10 without hindering the maintenance of the required traction.

In order to prevent the long member 35 from sliding out of engagement with the guide channel 33, the portable cervical traction device 10 includes a plurality of latches 50 pivotally attached along the length of one of the rails 32. Each latch 50 includes a hook section 51 selectively engaging corresponding lock pegs, dowels or posts 52 attached to the other rail 32 when in the closed/locked position. When the latches 50 are in the closed/locked position, the body of the latches 50 covers the open side of the guide channel 33 thereby confining movement of the traction bar 34 to the vertical and preventing any inadvertent movement of the traction bar 34 out of engagement within the guide channel 33.

Figure 5:
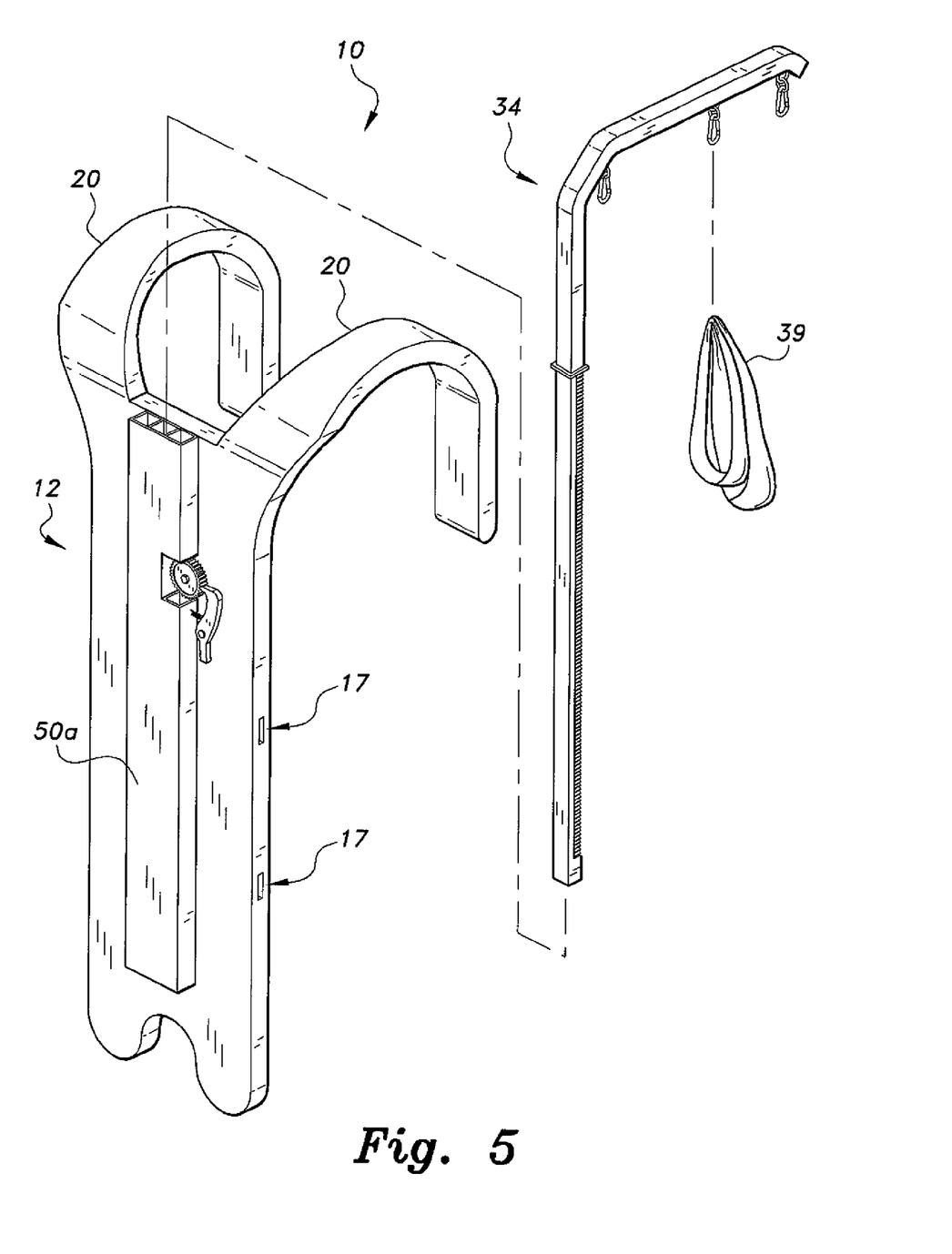
FIG. 5 is a perspective view of a cover for the guide rail on the portable cervical traction device according to the present invention.

As an alternative to the above, the portable cervical traction device 10 can be provided with a cover 50a as shown in FIG. 5. The cover 50a is preferably an elongate, channeled tubular member having a C-shaped cross section, the cover 50a being selectively mountable over the rails 32, 32 and secured to the back section 14. When installed, the cover 50a functions the same as the latches 50. As a further alternative, the cover 50a can be provided to cover both the rails 32, 32 and the latches 50 as a redundant component for confining the movement and preventing potential disengagement of the traction bar 34.

Figure 4A:
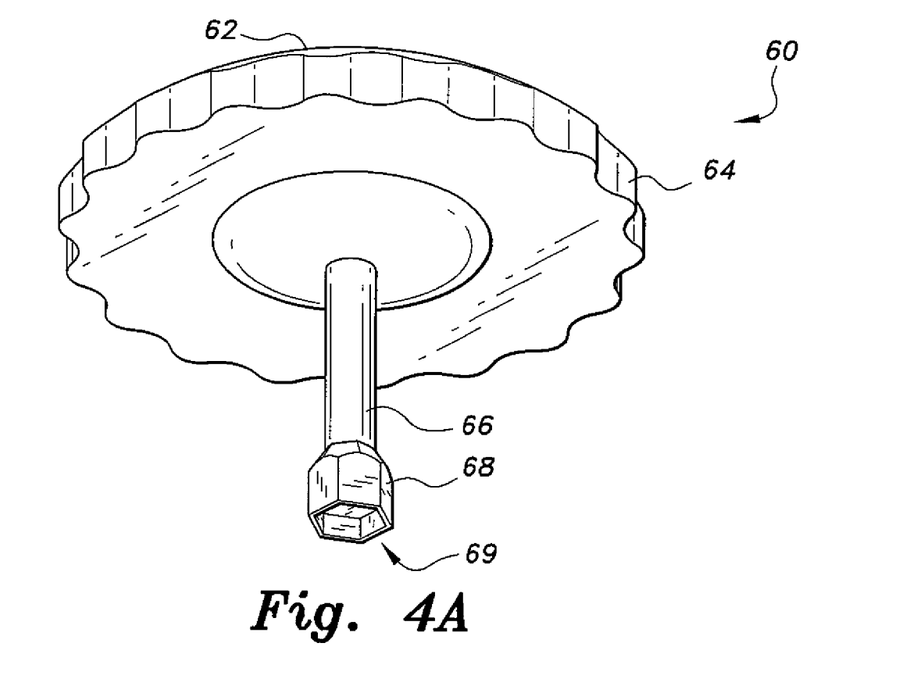
FIG. 4A is a bottom perspective view of a crank knob for a portable cervical traction device according to the present invention.
Figure 4B:
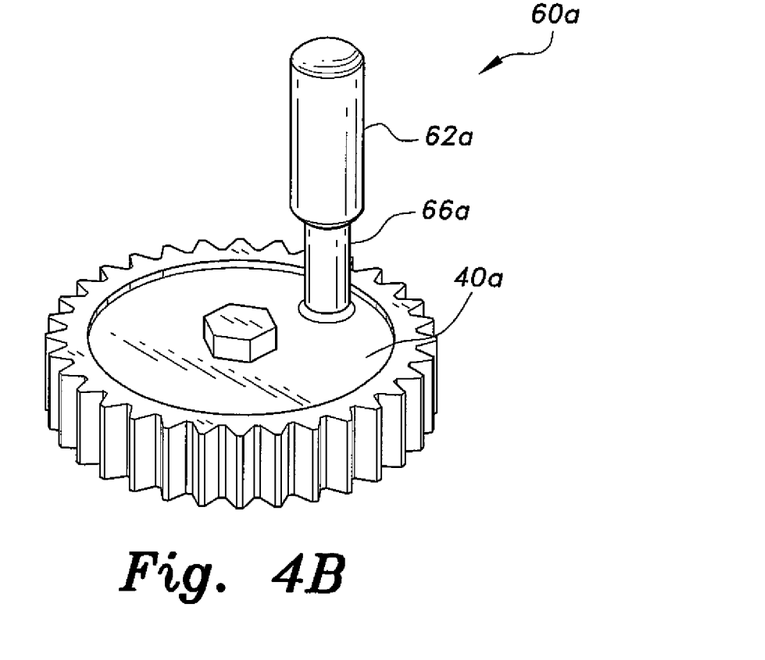
FIG. 4B is a top perspective view of an alternative pinion with a handle for a portable cervical traction device according to the present invention.

Referring to FIGS. 4A and 4B, the drawings depict some examples of means for rotating the drive pinion 40. In the embodiment described above with respect to FIGS. 1-3, the drive pinion 40 includes a raised boss, such as a hex-head, for a tool, e.g., a conventional hex-head wrench. The user can use such a tool to rotate the drive pinion 40. An alternative drive tool 60 is shown in FIG. 4A. In this exemplary embodiment, the drive tool 60 includes a circular, turning knob 62 sized to fit comfortably in the user's hand. A corrugated edge 64 can be provided around the circumference of the knob 62 to enhance the grip of the user during the turning operation of the knob 62. The knob 62 can also be provided with various other grip enhancing features, such as rubber coatings, various protrusions/indentions, and the like. An elongate shaft 66 extends from the bottom of the knob 62, terminating at a tool head 68 at the distal end. In this embodiment, the tool head 68 can be constructed as a hexagonal socket 69 for selective placement over the hex-head 41. Once engaged, the user rotates the knob 62 in either direction to raise or lower the traction bar 34. As an alternative, the hex-head on the drive pinion 40 can be replaced with a socket, and the tool head 68 can be constructed as a corresponding shaft or bit insertable into the socket.

A further exemplary arrangement for rotating the drive pinion is shown in FIG. 4B. In this embodiment, the drive pinion 40a includes a crank mechanism 60a. The crank mechanism 60a includes an elongate shaft 66a extending axially from a face of the drive pinion 40a. An elongate handle portion 62a extends contiguously from the shaft 66a. The shaft 66a is offset from the axis of the drive pinion 40a and rotatable with respect to the drive pinion 40a. This construction provides a crank arm for generating momentum. In use, the user grasps the handle portion 62a and turns the handle portion 62a about the axis of the drive pinion 40a. This forces the drive pinion 40a to rotate, thereby raising or lowering the traction bar 34.

Figure 6:
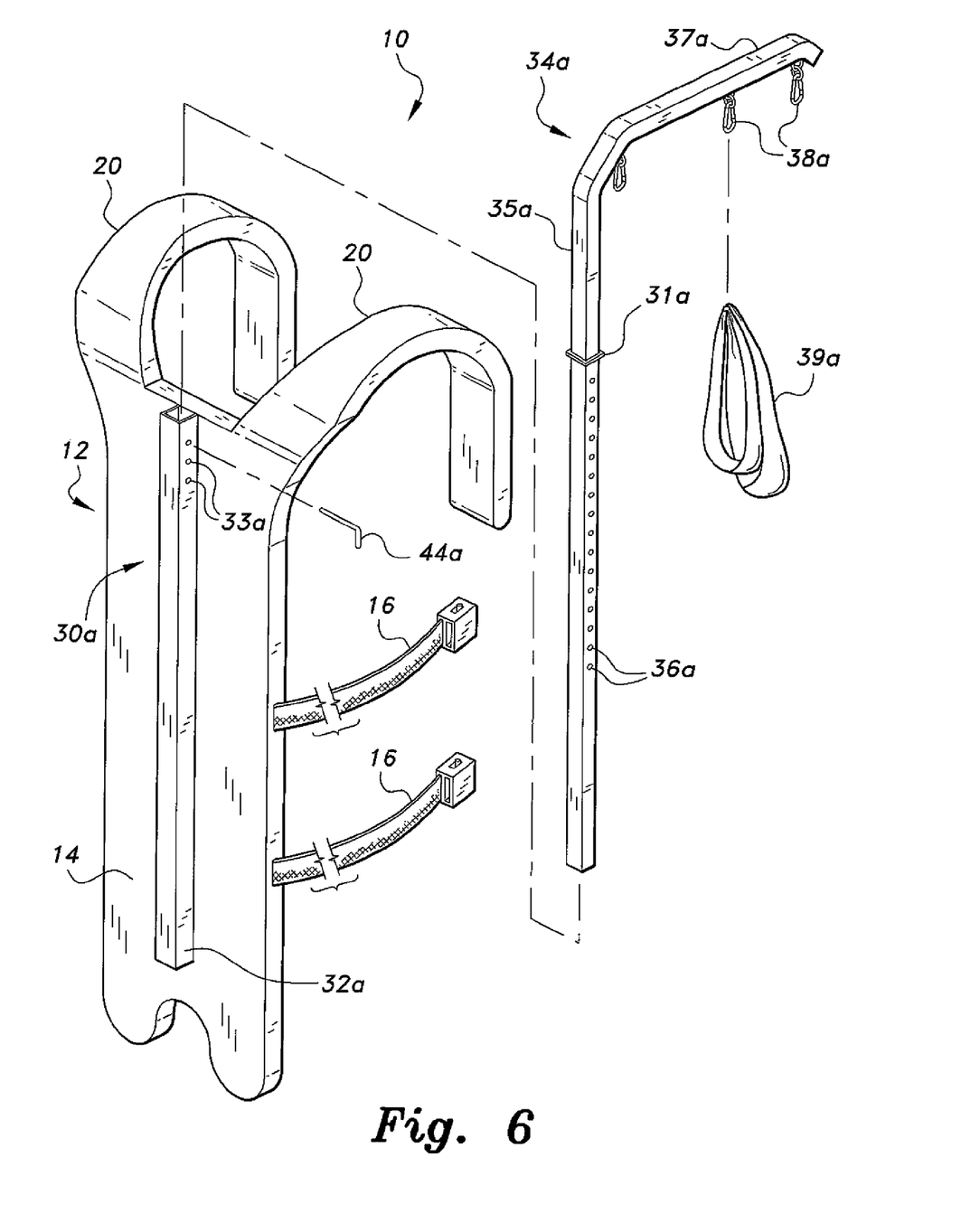
FIG. 6 is a partially exploded perspective view of an alternative embodiment of an adjustable traction control mechanism for a portable cervical traction device according to the present invention.

An alternative adjustable traction control mechanism 30a is shown in FIG. 6. In this embodiment, the rack and pinion is replaced with a relatively simpler means for setting the height of the traction bar 34a. As shown, the traction bar 34a is substantially the same as the previously described traction bar 34 and includes a cross member 37a, a plurality of hooks 38a, a head sling 39a, and a long member 35a. Instead of a rack section, the long member 35a is provided with a plurality of adjustment holes 36a disposed along the length of the long member 35a. An elongate guide sleeve 32a is disposed on the back section 14. The guide sleeve 32a includes at least one adjustment locking hole 33a on a side thereof. The long member 35a is insertable into the guide sleeve 32a, and an abutment flange or stop flange 31a disposed above the vertical row of adjustment holes 36a limits the extent of insertion of the long member 35a.

In use, the user slides or telescopes the long member 35a up or down within the guide sleeve 32a until the desired height of the traction bar 34a has been reached. The user aligns the adjustment hole 36a with a corresponding adjustment locking hole 33a at the adjusted position and set/locks the adjusted position with a locking pin 44a inserted through the aligned holes. This arrangement permits relatively quick height adjustments at set intervals defined by the spacing of the adjustment holes 36a. The intervals can be varied by changing the spacing of the adjustment holes 36a.

Figure 7A:
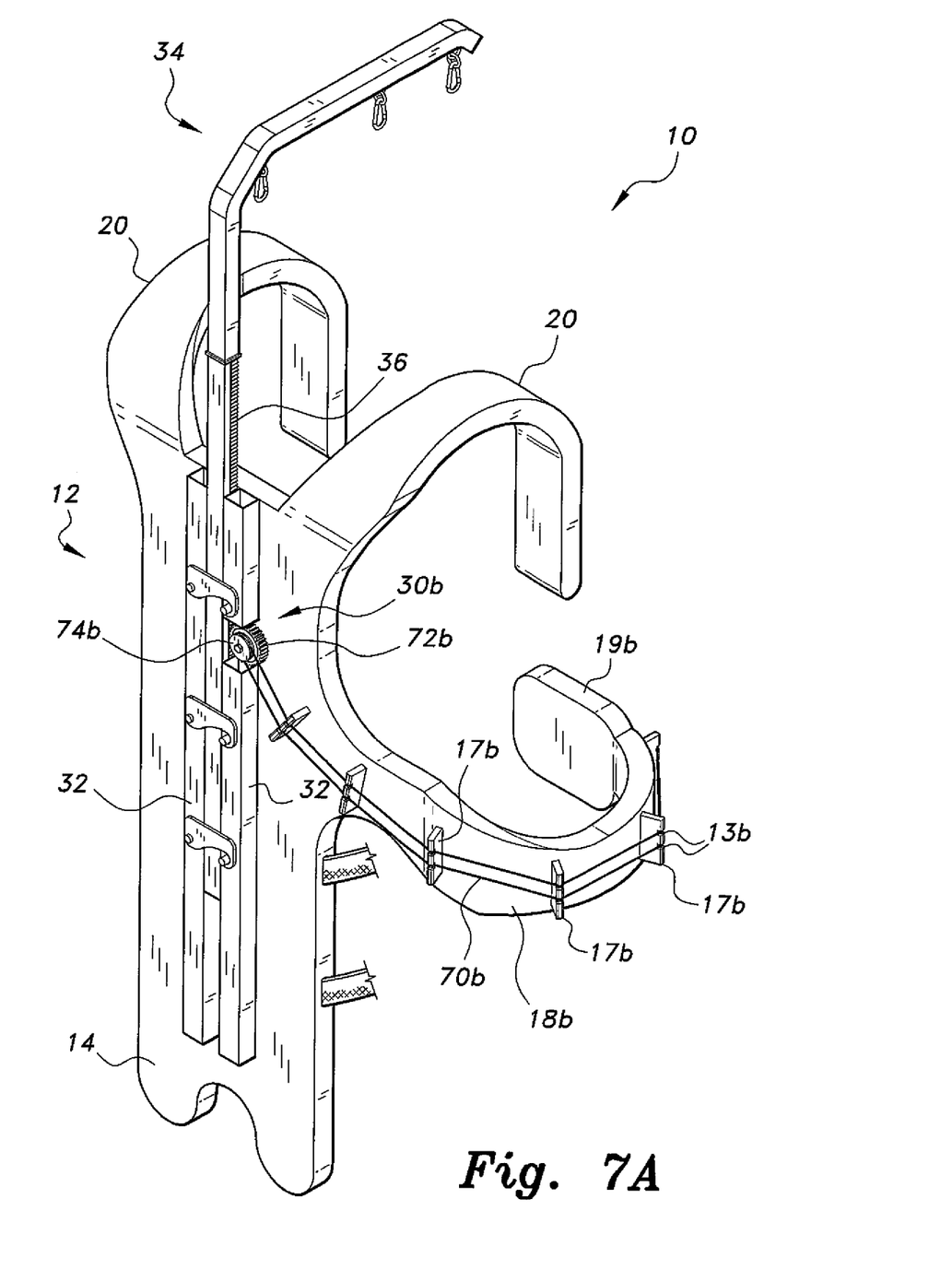
FIG. 7A is a front perspective view of an alternative embodiment of a traction control mechanism for the portable cervical traction device according to the present invention.
Figure 7B:
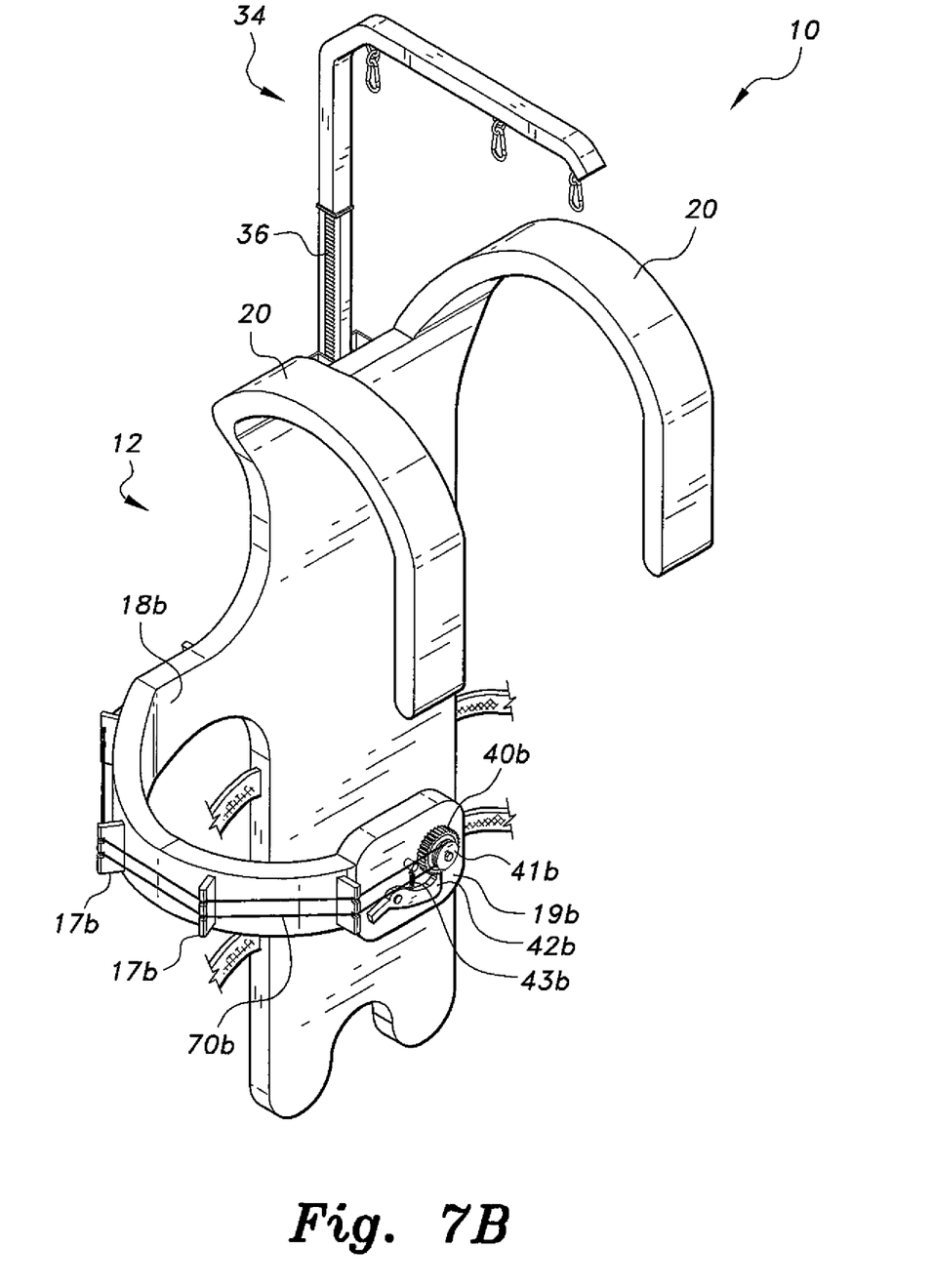
FIG. 7B is a back perspective view of the alternative traction control mechanism device of FIG. 7A.

A further alternative embodiment of an adjustable traction control mechanism 30b is shown in FIGS. 7A and 7B. This embodiment is substantially similar to the traction control mechanism 30 described above with respect to FIGS. 1-3, but it provides easier user access to the drive pinion for the user to facilitate the adjustments.

As shown, the adjustable traction control mechanism 30b includes a lateral torso strap, loop or hook 18b extending from one of the sides of the back section 14. In use, the torso hook 18b wraps around one of the sides of the user's torso and includes a control plate 19b at the distal end of the torso hook 18b. The placement of the torso hook 18b and the control plate 19b is constructed to provide easy access or reach of adjustment controls at the front of the user, instead of at the user's back, as in the previous embodiments.

In order to facilitate selective raising and lowering adjustment of the traction bar 34, the adjustable traction control mechanism 30b includes a pulley system accessible from the control plate 19b. The pulley system includes a drive wheel 41b attached to a drive pinion 40b and rotatable therewith. The drive pinion 40b is rotatably mounted to the control plate 19b, and the rotated position of the drive pinion 40b is locked or set by a biased pawl 42b, which is also pivotally mounted to the control plate 19b and biased by a spring 43b. Rotation of the drive pinion 40b or the drive wheel 41b can be facilitated by any of the means described above with respect to FIGS. 4A and 4B, and any variations thereof.

A cable 70b is trained around the drive pulley 41b and threaded around the torso hook 18b back towards a driven wheel 74b attached to a driven pinion 72b and rotatable therewith. A plurality of cable bridges 17b is disposed around the outer surface of the torso hook 18b. These cable bridges 17b serve to suspend the cable 70b above the surface of the torso hook 18b, which prevents potential entanglements and undue wear. At least a pair of pass-through gaps 13b for the cable 70b is formed on each cable bridge 17b to maintain separation of the cable 70b and proper trained engagement between the drive wheel 41b and the driven wheel 74b. The teeth of the driven pinion 72b engage the teeth on the rack section 36.

In use, the user rotates the drive wheel 41b from the front of the user with any of the means noted above. Rotation of the drive wheel 41b correspondingly rotates the driven wheel 74b via the cable 70b. This causes the driven pinion 72b to concurrently rotate, thereby raising or lowering the traction bar 74 to the desired height.

Figure 8A:
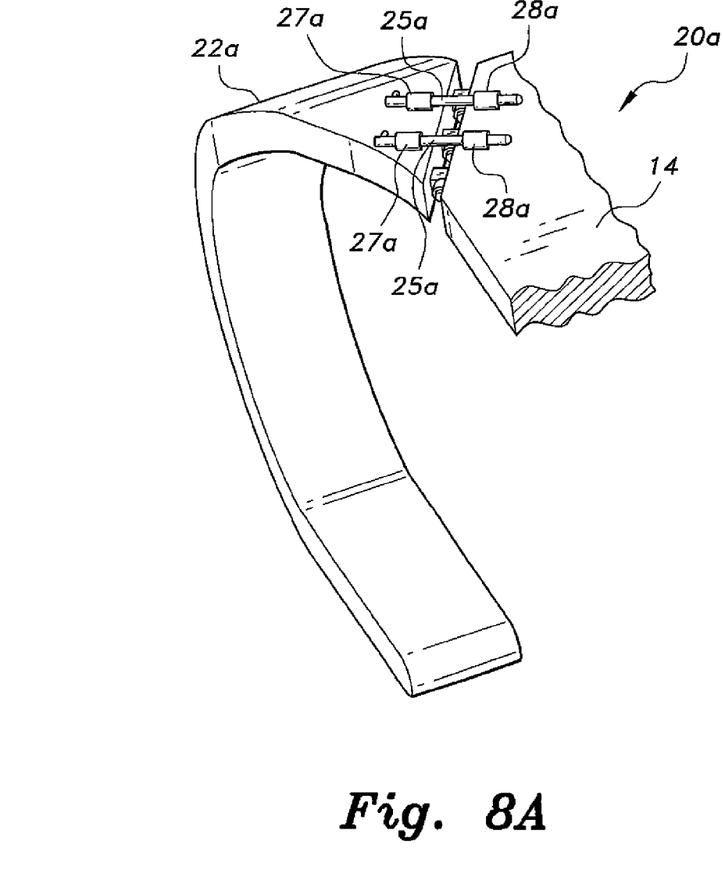
FIG. 8A is a perspective view of an alternative embodiment of a removable shoulder strap for the portable cervical traction device according to the present invention, the back portion of the brace being removed for clarity.
Figure 8B:
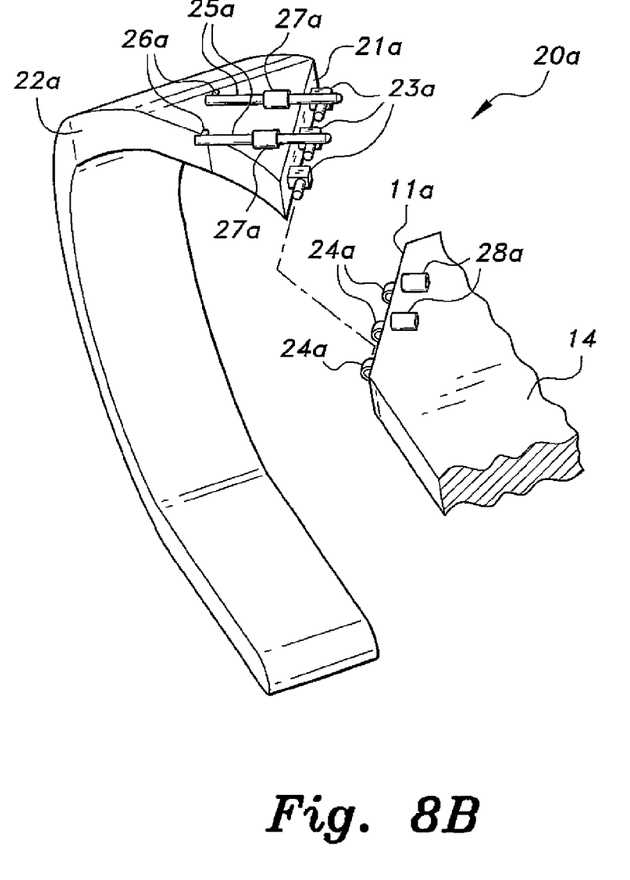
FIG. 8B is a partial exploded view of the removable shoulder strap of FIG. 8A.

An alternative shoulder strap, loop or hook 20a is shown in FIGS. 8A and 8B. In this embodiment, the shoulder hook 20a is detachable for ease of storage and/or packaging. It is noted that in these drawings, majority of the back section 14 has been removed for clarity.

As shown, the shoulder hook 20a includes a detachable hook section 22a that is detachably mounted to a corner of the back section 14. The mounting for the hook section 22a includes a plurality of mounting hooks 23a disposed on an end face 21a of the hook section 22a. These mounting hooks 23a are insertably mounted to corresponding loops 24a disposed on an end face 11a of back section 14. When assembled, the end face 21a and end face 11a face each other. The engagement of the mounting hooks 23a with the loops 24a provides an initial or first stage connection between the hook section 22a and the back section 14 along one direction.

The shoulder hook 20a also includes at least a pair of elongate locking pins 25a for selective insertion through locking loops 27a on the hook section 22a and locking loops 28a on the back section 14. After the initial connection has been established, installation of the locking pins 25a through the locking loops 27a, 28a secures the connection between the hook section 22a and the back section 14 by establishing a connection in a perpendicular direction from the initial connection. As can be seen from the drawings, the initial connection is not so secure that it prevents rotation or pivoting of the hook section 22a with respect to the back section 14 and vice versa, especially during use. This can lead to possible disengagement of the components. However, the additional connection established by the locking pins 25a prevents this undesirable pivoting movement as well as the potential disengagement. Each locking pin 25a can be provided with an outwardly extending extension or protrusion 26a to assist the user in manipulating the locking pins 25a.

It is to be noted that the portable cervical traction device 10 encompasses a variety of alternatives. For example, although the drawings depict the traction bar 34 as square-shaped in cross section, the traction bar 34 can be constructed in various geometric shapes in cross section as well as the overall shape of the traction bar 34 so long as the head sling 39 can be hung at various locations thereon and securely reciprocate in a correspondingly shaped guide channel 33. Moreover, the shoulder hook 20 can be constructed as an adjustable loop in a similar manner to backpack shoulder straps.

It is to be understood that the present invention is not limited to the embodiments described above, but encompasses any and all embodiments within the scope of the following claims.

I claim:

1. A portable cervical traction device, comprising:
  a brace having an elongate back section and a pair of detachable shoulder hooks extending from the back section, the brace being adapted to be worn over the shoulders and back of a user;
  a mounting for detachably mounting each of the detachable shoulder hooks to respective corners of the back section, consisting of;
    a hook section having an end face;
    a plurality of mounting hooks disposed on the end face of the hook section, each corner of the back section having an end face and a plurality of loops, the plurality of mounting hooks being insertable into the plurality of loops on the corner of the back section to form an initial connection;
    at least one locking loop disposed on the hook section;
    at least one locking loop disposed on the back section, the at least one locking loop on the back section corresponding to and being aligned with the at least one looking loop on the hook section when assembled; and
    at least one locking pin insertable through the at least one locking loop on the hook section and the corresponding locking loop on the back section, the locking pin establishing a final connection for securely mounting the hook section to the corner of the back section, the at least one locking pin each having an outwardly extending protrusion for assisting the user in manipulating the at least one locking pin;
  a traction control mechanism attached to the back section for adjustably applying traction on the user, the traction control mechanism having an elongate, vertical traction bar extendable along the back section and means for selectively raising and lowering the elongate, vertical traction bar, the elongate, vertical traction bar having a plurality of hooks thereon and a head sling selectively hung on at least one of the plurality of hooks on the traction bar for comfortably supporting the user's head during traction; and
  at least one releasable strap attached laterally to the back section, the at least one releasable strap securing the brace around the user's torso.

2. The portable cervical traction device according to claim 1, wherein the traction control mechanism comprises:
   a pair of spaced, elongate vertical rails attached to the back section, the pair spaced, elongate vertical rails defining a guide channel therebetween, the elongate, vertical traction bar being slidably engaged within the guide channel; and
   means for preventing disengagement of the elongate, vertical traction bar from the guide channel, the means for preventing disengagement being disposed on the pair spaced, elongate vertical rails.

3. The portable cervical traction device according to claim 2, wherein the means for preventing disengagement comprises:
   a plurality of latches pivotally mounted along the length of one of the pair of rails, each of the latches having a body and a hook section; and
   a plurality of lock posts mounted to the other of the pair of rails, each of the latches selectively hooking onto a corresponding one of the lock posts, thereby positioning the body of the latch across the guide channel in order to block potential movement of the traction bar out of engagement therewith.

4. The portable cervical traction device according to claim 2, wherein the means for preventing disengagement comprises a cover selectively placed over the pair spaced, elongate vertical rails, the cover enclosing the guide channel in order to block potential movement of the elongate, vertical traction bar out of engagement therewith.

5. The portable cervical traction device according to claim 2, wherein the elongate, vertical traction bar comprises an L-shaped bar having a long member and a cross member, the plurality of hooks being disposed along the cross member, the long member having an elongate rack gear section.

6. The portable cervical traction device according to claim 5, wherein the means for selectively raising and lowering the elongate, vertical traction bar comprises:
   a drive pinion rotatably mounted in a gap on one of the rails, the drive pinion having teeth engaged with teeth on the rack gear section of the elongate, vertical traction bar, selective rotation of the drive pinion raising and lowering the elongate, vertical traction bar via the rack gear section;
   a pawl pivotally mounted to the back section adjacent the drive pinion; and
   a spring attached to the pawl and the back section, the pawl being biased by the spring and selectively engaging the teeth on the drive pinion at each rotated position of the drive pinion in order to raise and lower the elongate, vertical traction bar.

7. The portable cervical traction device according to claim 6, further comprising a turning tool for selectively turning the drive pinion.

8. The portable cervical traction device according to claim 7, wherein:
   the turning tool comprises a circular knob having corrugations around the circumference thereof for enhancing grip during use, an elongate shaft extending from a bottom of the knob, and a tool head at a distal end of the shaft, the tool head having a socket;
   the drive pinion has a shaped, raised boss, the socket of the tool head being selectively engageable with the raised boss in order to facilitate rotation of the drive pinion upon turning of the knob.

9. The portable cervical traction device according to claim 5, further comprising a crank handle rotatably mounted to a face of the drive pinion, the crank handle being offset from an axis of rotation of the drive pinion.

10. The portable cervical traction device according to claim 5, wherein the means for selectively raising or lowering the elongate, vertical traction bar comprises:
    a torso hook extending from a side of the back section, the torso hook having an outer surface and a control plate at a distal end thereof, the torso hook being adapted for wrapping around a side of the user; and
    a pulley system mounted between the control plate and one of the pair spaced, elongate vertical rails;
    wherein the control plate permits easy access for selective operation of the pulley system in front of the user when the brace is worn, selective operation of the pulley system raising or lowering the elongate, vertical traction bar.

11. The portable cervical traction device according to claim 10, wherein the pulley system comprises:
    a drive pinion rotatably mounted to the control plate, the drive pinion having teeth;
    a drive wheel coaxially mounted to the drive pinion and rotatable therewith;
    a pawl pivotally mounted to the control plate adjacent the drive pinion; a spring attached to the pawl and the control plate, the pawl being biased by the spring and selectively engaging the teeth on the drive pinion at each rotated position of the drive pinion in order to fix the desired height of the elongate, vertical traction bar;
    a driven pinion rotatably mounted in a gap on one of the pair spaced, elongate vertical rails, the driven pinion having teeth engaged with teeth on the rack gear section of the elongate, vertical traction bar;
    a driven wheel coaxially mounted to the driven pinion and rotatable therewith;
    a cable trained around the drive wheel and the driven wheel; and
    a plurality of cable bridges attached to the torso hook, each cable bridge having at least two pass-through gaps formed thereon, the pass-through gaps suspending the cable above the outer surface of the torso hook, the pass-through gaps maintaining separation of the cable and proper trained engagement between the drive wheel and the driven wheel; wherein selective rotation of the drive wheel rotates the driven wheel to thereby rotate the driven pinion in order to raise or lower the elongate, vertical traction bar through mutual engagement between the rack gear section and the driven pinion.

12. The portable cervical traction device according to claim 2, wherein the elongate, vertical traction bar comprises an L-shaped bar having a long member and a cross member, the plurality of hooks being disposed along the cross member, the long member having a plurality of adjustment holes formed on a side thereof at preselected intervals and a stop flange disposed above the plurality of adjustment holes.

13. The portable cervical traction device according to claim 12, wherein the means for selectively raising or lowering the elongate, vertical traction bar comprises:
    an elongate, vertical guide sleeve attached to the back section, the guide sleeve having at least one locking hole formed on a side thereof, the long member of the elongate, vertical traction bar being slidably mounted in the guide sleeve, the stop flange limiting extent of insertion of the long member; and
    at least one locking pin selectively insertable through the at least one locking hole and one of the adjustment holes on the long member when aligned with the at least one locking hole;

wherein slidable extension or retraction of the long member within the guide sleeve adjusts height by raising and lowering the elongate, vertical traction bar, the adjusted height being locked by aligning one of the adjustment holes with the at least one locking hole and inserting the locking pin through the aligned holes.

14. The portable cervical traction device according to claim 1, further comprising padding disposed on the brace.

15. A cervical traction device, comprising:
a brace having an elongate back section, a pair of shoulder hooks extending from the back section, padding disposed on the brace, and at least one selectively releasable securing strap attached laterally to the brace;
a traction control mechanism attached to the back section, for adjustably applying traction, having an L-shaped bar coupled to the back section, and a means for selectively raising and lowering the L-shaped bar;
wherein the L-shaped bar includes a vertical portion having a first end extending along the back section and a horizontal portion extending from a second end of the vertical portion, the horizontal portion includes a plurality of books disposed thereon, and the vertical portion includes a rack gear section;
the means for selectively raising and lowering the L-shaped bar including:
a pair of spaced, elongate vertical rails attached to the back section, the pair spaced, elongate vertical rails defining a guide channel therebetween, the first end of the vertical portion being slidably engaged within the guide channel;
a torso hook extending from a side of the back section, the torso hook having an outer surface and a control plate at a distal end thereof;
a drive pinion rotatably coupled the brace for driving the rack gear section of the vertical portion;
a pulley system mounted between the control plate and one of the pair spaced, elongate vertical rails, pulley system operatively coupled to the drive pinion;
wherein selective rotation of the drive pinion causing the selective raising and lowering of the L-shaped bar;
a spring biased pawl for maintaining the drive pinion at a preselected position, the preselected position being attained by selectively raising and lowering the L-shaped bar; and
a head sling selectively hung on at least one of the hooks of the horizontal portion.

16. The cervical traction device according to claim 15, wherein the traction control mechanism further including means for preventing disengagement of the traction bar from the guide channel, the means for preventing disengagement being disposed on the rails; and
wherein the pulley system of the means for selectively raising and lowering the L-shaped bar comprising:
a driver pinion rotatably mounted to the control plate, the driver pinion having teeth;
a driver wheel coaxially mounted to the drive pinion and rotatable therewith;
a driven wheel coaxially mounted to the drive pinion and rotatable therewith;
a cable coupled between the driver wheel and the driven wheel; and
a plurality of cable bridges attached to the torso hook, each cable bridge having at least two pass-through gaps formed thereon, the pass-through gaps suspending the cable above the outer surface of the torso hook, the pass-through gaps maintaining separation of the cable and proper engagement between the drive wheel and the driven wheel; wherein selective rotation of the driver pulley rotates the driven pulley to thereby rotate the drive pinion in order to raise or lower the traction bar through mutual engagement between the rack gear section and the driven pinion;
wherein the pawl being disposed at the driver pinion on the control plate.

17. The cervical traction device according to claim 16, further comprising padding disposed on the brace.

18. A portable cervical traction device, comprising:
a brace having an elongate back section and a pair of shoulder hooks extending from the back section;
a traction control mechanism attached to the back section for adjustably applying traction;
wherein the traction control mechanism comprising:
an elongate, vertical L-shaped traction bar having a long member and a cross member, the long member of the elongate, vertical L-shaped traction bar extending along the back section, and the cross member of the elongate, vertical L-shaped traction bar having a plurality of hooks disposed there along;
a head sling selectively hung on at least one of the hooks on the cross member for head support during traction;
a pair of spaced, elongate vertical rails attached to the back section, the pair spaced, elongate vertical rails defining a guide channel therebetween, the long member extending between the pair spaced, elongate vertical rails;
means coupled to the rails for preventing disengagement of the long member of the elongate, vertical L-shaped traction bar from the guide channel; and
means for selectively raising and lowering the elongate, vertical L-shaped traction bar including an elongate rack gear section extending along the long member;
a torso hook extending from a side of the back section, the torso hook having an outer surface and a control plate at a distal end thereof; and
a pulley system mounted between the control plate and one of the pair spaced, elongate vertical rails;
wherein the control plate permits easy access for selective operation of the pulley system in front of the user when the brace is worn, selective operation of the pulley system raising or lowering the elongate, vertical L-shaped traction bar; and
at least one releasable strap attached laterally to the back section, the releasable straps securing the brace around a torso.

19. The portable cervical traction device according to claim 18, wherein the pulley system comprises:
a drive pinion rotatably mounted to the control plate, the drive pinion having teeth;
a drive wheel coaxially mounted to the drive pinion and rotatable therewith;
a pawl pivotally mounted to the control plate adjacent the drive pinion;
a spring attached to the pawl and the control plate, the pawl being biased by the spring and selectively engaging the teeth on the drive pinion at each rotated position of the drive pinion in order to fix the desired height; of the elongate, vertical L-shaped traction bar
a driven pinion rotatably mounted in a gap on one of the pair spaced, elongate vertical rails, the driven pinion having teeth engaged with teeth on the rack gear section of the traction bar;
a driven wheel coaxially mounted to the driven pinion and rotatable therewith;

a cable trained around the drive wheel and the driven wheel; and a plurality of cable bridges attached to the torso hook, each cable bridge having at least two pass-through gaps formed thereon, the pass-through gaps suspending the cable above the outer surface of the torso hook, the pass-through gaps maintaining separation of the cable and proper trained engagement between the drive wheel and the driven wheel; wherein selective rotation of the drive wheel rotates the driven wheel to thereby rotate the driven pinion in order to raise or lower the elongate, vertical L-shaped traction bar through mutual engagement between the rack gear section and the driven pinion.

20. The portable cervical traction device according to claim 19, further comprising padding disposed on the brace.

\* \* \* \* \*